US008663668B2

(12) United States Patent
Leinenbach et al.

(10) Patent No.: US 8,663,668 B2
(45) Date of Patent: Mar. 4, 2014

(54) PRESERVATIVE FOR MEDICAL DEVICES

(75) Inventors: Hans-Peter Leinenbach, Tholey (DE); Stefan Kuhn, Neunkirchen (DE); Ute Gabsdil, Wiesloch (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1209 days.

(21) Appl. No.: 11/596,352

(22) PCT Filed: May 4, 2005

(86) PCT No.: PCT/EP2005/004836
§ 371 (c)(1),
(2), (4) Date: Nov. 14, 2006

(87) PCT Pub. No.: WO2005/110498
PCT Pub. Date: Nov. 24, 2005

(65) Prior Publication Data
US 2007/0196328 A1 Aug. 23, 2007

(30) Foreign Application Priority Data
May 14, 2004 (DE) .......................... 10 2004 024 140

(51) Int. Cl.
*A01N 25/00* (2006.01)
*A01N 43/38* (2006.01)

(52) U.S. Cl.
USPC .......................................... 424/405; 514/419

(58) Field of Classification Search
None
See application file for complete search history.

(56) References Cited

U.S. PATENT DOCUMENTS

| 4,702,829 | A | * | 10/1987 | Polaschegg et al. ....... 210/195.2 |
| 5,078,967 | A | | 1/1992 | Riera Aixala |
| 5,192,459 | A | | 3/1993 | Tell et al. |
| 5,498,416 | A | | 3/1996 | Carsenti-Etesse et al. |
| 6,174,537 | B1 | | 1/2001 | Khan |
| 6,350,251 | B1 | | 2/2002 | Prosl et al. |
| 6,423,024 | B1 | * | 7/2002 | Strom et al. ...................... 604/8 |
| 6,762,206 | B2 | | 7/2004 | Khan |
| 2004/0034042 | A1 | * | 2/2004 | Tsuji et al. ............... 514/263.31 |
| 2004/0185028 | A1 | | 9/2004 | Hu et al. |

FOREIGN PATENT DOCUMENTS

| DE | 35 37 627 A1 | 5/1986 |
| DE | 195 03 613 | 3/1996 |
| DE | 195 15 428 C2 | 11/1996 |
| DE | 100 48 391 A1 | 4/2002 |
| EP | 0 222 146 A2 | 5/1987 |
| EP | 0 450 117 A1 | 10/1991 |
| EP | 0 700 249 | 3/1996 |
| EP | 1 192 860 A1 | 4/2002 |
| EP | 1192860(A1) | 4/2002 |
| GB | 1 533 255 | 11/1978 |
| GB | 1533255(A) | 11/1978 |
| JP | 52151294(A) | 12/1977 |
| WO | WO 94/27440 | 12/1994 |
| WO | WO 00/18442 | 4/2000 |
| WO | WO 00/27439 | 5/2000 |
| WO | WO 0033829 A1 * | 6/2000 |
| WO | WO 00/62 618 | 10/2000 |
| WO | WO 02/051464 A2 | 7/2002 |

OTHER PUBLICATIONS tryptophan, http://omlc.ogi.edu/spectra/PhotochemCAD/html/tryptophan.html, 1-2.*
tryptophan, http://omlc.ogi.edu/spectra/PhotochemCAD/html/tryptophan.html, 2 pages, Feb. 1995 (prevously cited Jul. 30, 2009).*
Zhang Y., et al., "Synthesis and Anitmicrobial Activity of Polymeric Guanidine and Biguanidine Salts", Polymer, Elsevier Science Publishers B.V., GB, vol. 40, No. 22, Oct. 1999 (no copy available).

* cited by examiner

*Primary Examiner* — Kyle Purdy
(74) *Attorney, Agent, or Firm* — Jacobson Holman PLLC

(57) ABSTRACT

The invention relates to the field of disinfection and preservation of surfaces of medical devices. The object of the invention is to make available a disinfectant that provides effective decontamination of medical devices while at the same time being toxicologically safe. This object is achieved through the use of solution containing biguanide. Additional advantages of using such solutions include the fact that the active ingredient used for preservation can be completely rinsed out prior to use and does not have a negative effect on the functionality of protein-containing medical devices. The thoroughness of the rinsing operation can be verified by means of a spectroscopically active additive.

16 Claims, No Drawings

PRESERVATIVE FOR MEDICAL DEVICES

This is a nationalization of PCT/EP05/004836 filed May 4, 2005 and published in German.

The present invention relates to the field of disinfection and preservation of surfaces of medical equipment, in particular medical equipment for use in extracorporeal blood circulation systems.

Various medical devices come in contact with biological fluids during use. This is the case in particular with medical devices used in the extracorporeal blood circulation. These devices include, for example, dialyzers, blood filters and adsorbers. In all cases in which a fluid is re-infused into humans or animals after coming in contact with the medical device, it is essential for the surface coming in contact with the fluid to be free of pathogens. In most cases, this is achieved by heat sterilization of the medical device. In other cases, heat sterilization cannot be performed effectively because the functionality of the medical device would be impaired by such sterilization. This is the case with adsorbers in particular which have proteins bound as ligands.

Such adsorbers of this type are known from the state of the art. For example, EP 0 222 146 describes an adsorbent for removal of antigen-antibody complexes. The protein C1q functions as the ligand here.

Hemodialyzers are sometimes reused after the first treatment. Even in these cases, it is necessary to regenerate the dialyzer through effective decontamination prior to the next use. This may be performed by washing with a disinfectant as described in U.S. Pat. No. 5,192,459. The various acids are proposed as disinfectants. In WO 00/27439, however, oxidizing agents are used in the presence of urea as a disinfectant.

None of the aforementioned methods can be used for effective decontamination of a protein-containing adsorbent while maintaining functionality, however. In the past, agents containing heavy metals or sodium azide and thus having a low biocompatibility have been used for this purpose. The complex complete removal of these disinfectants according to the state of the art is therefore absolutely essential prior to use of the medical device.

The object of the present invention is to make available a disinfectant and preservative that permits effective decontamination of medical devices, in particular medical devices for use in an extracorporeal circulation, while at the same time being toxicologically safe.

These objects are achieved according to this invention by using a solution containing biguanide according to claim 1. Additional advantageous embodiments are the subject matter of the subclaims.

This invention is based on the surprising finding that solutions containing a biguanide compound are excellently suitable for disinfection of medical devices for use in an extracorporeal blood circulation. These solutions, which have previously been used as wound antiseptics and preservatives for ophthalmic preparations are characterized by an excellent biocompatibility and a low toxicity for humans. Nevertheless, the solution may achieve comparable or even better results in disinfection and preservation of the aforementioned medical equipment than the substances which have a higher toxicity and have been used previously in the state of the art.

Solutions containing biguanides are known as wound antiseptics in the state of the art (EP 0 450 117). The use of biguanides for coating medical devices for extracorporeal treatment is described in EP 0 456 093. Poly(hexamethylene) biguanide, which has a molecular weight of 2900 to 15,000, is mentioned in EP 0700249 as being an especially effective disinfectant. This anti-infective agent is also distributed for wound treatment by the company Fresenius Kabi under the brand name LAVASEPT®. Another known use of such a solution is for disinfection and preservation of contact lenses.

Within the context of the present invention, preferably poly(hexamethylene)biguanide having a molecular weight of 2900 to 15,000 (PHMB) is used as the biguanide compound. An especially preferred disinfection solution contains PHMB in a concentration of 0.01% to 0.5% by weight, where concentrations of 0.02% to 0.06% by weight are especially advantageous. A neutral buffer containing phosphate, and preferably also containing the following substances is used as the medium: sodium citrate dihydrate, sodium acetate trihydrate, sodium chloride, sodium monohydrogen phosphate, potassium dihydrogen phosphate. Such a solution effectively disinfects and preserves the aforementioned medical devices and is in compliance with the requirements of the "antimicrobial effectiveness tests" described in USP 27 (United States Pharmacopoeia).

Another important advantage of the inventive approach is that the functionality of proteins is preserved. In addition, it has been demonstrated that after filling a protein-containing adsorber with the solution described above as a preservative agent prior to a storage period of four weeks in the dark at a temperature of 37° C., there was no detectable loss of functionality of the proteins. In the case of storage at 4° C., much longer storage is possible without any loss of functionality. Therefore, the present invention also includes a method for disinfection and preservation of surfaces of a medical device using a solution according to claim 1 with the steps of filling the medical device with the solution containing a biguanide compound and to then store the medical device in a filled state.

In addition, another advantageous aspect of the inventive use of the solution is that the preservative can be completely rinsed out of the medical device prior to its use in an extracorporeal circulation. To check on the thoroughness of rinsing out the inventive solution according to claim 1, another aspect of the present invention is to add a nontoxic additive that can be detected spectroscopically to the solution. Therefore, this invention also includes a solution for disinfection or preservation of medical equipment characterized in that it contains a biguanide compound and a spectroscopically active nontoxic additive. In a particularly preferred embodiment, tryptophan in a concentration of at least 0.005% by weight is used as an additive. It is especially preferable to add tryptophan in a concentration of 0.01% to 0.1% by weight. Tryptophan absorbs UV light at a wavelength of 280 nm and a concentration determination may be performed spectroscopically in a solution on the basis of the Lambert-Beer law. Tryptophan itself does not have any disinfectant effect. It is therefore used exclusively to measure the progress of the rinsing operation and a preservative step which follows the treatment. Experiments have shown that tryptophan is removed from the column to the same extent as PHMB in the rinsing operation.

Examples that should contribute toward explaining the invention without restricting this invention in any way are presented below.

EXAMPLES

Example 1

Composition of the Solution

A solution containing the following ingredients is prepared as a disinfectant and preservative solution for an adsorber:

400 mg poly(hexamethylene)biguanide
300 mg tryptophan
3.3 g sodium citrate dihydrate
5.44 g sodium acetate trihydrate
4.92 g sodium chloride
2.9 g disodium hydrogen phosphate·$12H_2O$
260 mg potassium dihydrogen phosphate.

The ingredients are dissolved, the solution is adjusted to a pH of 7.0 and topped off to yield 1 L.

Example 2

Disinfectant Effect

An adsorber column of the type IMMUNOSORBA (Fresenius Adsorber Technology GmbH) is used to remove antibodies from blood plasma and binds the antibodies via protein A of *Staphylococcus aureus*. This adsorber column is filled with a solution according to Example 1. The disinfectant/preservative effect of the solution corresponds to the specifications of USP 27.

Example 3

Functionality Test after Storage

Adsorber columns filled according to Example 2 are stored in the absence of light for a long period of time. In storage at 40° C., no loss of functionality could be detected before a period of 4 weeks. After 35 weeks of storage at 37° C., the Ig binding capacity of the column for antibodies was reduced by 20%. In 46 weeks of storage at 4° C., the column filled according to Example 2 did not show any loss of functionality.

Example 4

Rinsability of the Preservative Solution

An adsorber column filled according to Example 2 is connected to an apparatus of type CITEM-10 (Fresenius Adsorber Technology). The column is rinsed out by a rinsing program provided with it.

To do so, first the column is rinsed with 300 mL of a buffer 1 having the following composition:
3.3 g sodium citrate dihydrate
5.44 g sodium acetate trihydrate
4.92 g sodium chloride
2.9 g disodium hydrogen phosphate·$12H_2O$
260 mg potassium dihydrogen phosphate
pH 7.0.

Then the column is rinsed with 100 mL of an eluent having the following composition:
3.3 g sodium citrate dihydrate
5.44 g sodium citrate trihydrate
4.92 g sodium chloride
2.9 g disodium hydrogen phosphate·$12H_2O$
260 mg potassium dihydrogen phosphate
pH 2.0
and then rinsed again with 350 mL more of buffer 1. After rinsing a treatment simulation was performed using 3 liters of blood plasma.

The process of rinsing out the preservative solution within the column preparation step was monitored by UV detection of the amino acid tryptophan using the CITEM 10 monitor.

The following results were observed:
a) At the end of the rinsing operation described above, no traces of PHMB were detected above the limit of detection (LOD of PHMB=0.90 mg/L).
b) Tryptophan concentrations between the lower limit of detection (2.2 ppm) and the tryptophan quantification limit (7.0 ppm) were detected in the treated plasma.
c) Approximately 20% more PHMB and approx. 8% more Trp were found in the rinsing solutions than the amount calculated by means of the assumed volume. In the subsequent tests, it was found that 20% PHMB and/or 8% Trp more remained in the columns during preservation. In addition, these tests revealed that these amounts could be rinsed out completely during the column preparation step.
d) Within the 20 treatment simulations, the CPI (Column Performance Index) remains stable at a high level (>35).
e) The binding capacity with respect to the antibody classes, IgG, IgM, IgA and subclass IgG3 remained stable.

Trp has an elution behavior very similar to that of PHMB and therefore is suitable for use as an indicator of the progress of the rinsing out of PHMB as well as preservation of the columns after the treatments.

No additional difference in the rinsing behavior of the new column and the column loaded with plasma could be ascertained.

The invention claimed is:

1. A method of disinfecting and preserving a surface of a protein-containing medical device selected from the group consisting of hemodialysers, blood filters, and adsorbers, wherein the medical device has proteins bound as ligands, comprising contacting the surface of the medical device with a solution containing biguanide to preserve the proteins' functionality.

2. The method of claim 1, wherein the biguanide compound is poly(hexamethylene)biguanide.

3. The method of claim 2, wherein the biguanide compound has a molecular weight $M_w$ of 2900 to 15,000.

4. The method of claim 1, wherein the solution has a concentration of the biguanide compound of 0.01 to 0.5% by weight.

5. The method of claim 1, wherein the solution contains tryptophan.

6. The method of claim 5, wherein the solution has a tryptophan concentration of at least 0.005% by weight.

7. The method of claim 1, wherein the medical device is suitable for use in extracorporeal blood circulation.

8. A method of disinfecting and preserving surfaces of a protein-containing medical device selected from the group consisting of hemodialysers, blood filters, and adsorbers, wherein the medical device contains proteins bound as ligands, comprising the following steps:
(1) filling the medical device with a solution containing a biguanide compound such that the surfaces are in contact with the solution; and
(2) storing the medical device containing the solution, while preserving the proteins' functionality.

9. The method according to claim 8, wherein the solution further comprising the step of rinsing the solution out of the medical device prior to the medical device being used.

10. The method according to claim 9, wherein the solution further contains a spectroscopically active nontoxic additive, and progress of the rinsing step is monitored by spectroscopic measurements of the spectroscopically active nontoxic additive in the solution after it has been rinsed out.

11. The method according to claim 10, wherein the additive is tryptophan.

12. The method according to claim 1, wherein the medical device is an adsorber.

13. The method according to claim 2, wherein the medical device is an adsorber.

14. The method according to claim 5, wherein the medical device is an adsorber.

15. The method according to claim 8, wherein the medical device is an adsorber.

16. The method according to claim 10, wherein the medical device is an adsorber.

\* \* \* \* \*

UNITED STATES PATENT AND TRADEMARK OFFICE
CERTIFICATE OF CORRECTION

PATENT NO.       : 8,663,668 B2
APPLICATION NO.  : 11/596352
DATED            : March 4, 2014
INVENTOR(S)      : Leinenbach et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1332 days.

Signed and Sealed this
Twenty-ninth Day of September, 2015

Michelle K. Lee
*Director of the United States Patent and Trademark Office*